United States Patent
Matsuura

(10) Patent No.: US 11,454,592 B2
(45) Date of Patent: Sep. 27, 2022

(54) CONFIRMATION APPARATUS, CONFIRMATION METHOD, AND NON-TRANSITORY STORAGE MEDIUM

(71) Applicant: NEC CORPORATION, Tokyo (JP)

(72) Inventor: Hiroki Matsuura, Tokyo (JP)

(73) Assignee: NEC CORPORATION, Tokyo (JP)

( * ) Notice: Subject to any disclaimer, the term of this patent is extended or adjusted under 35 U.S.C. 154(b) by 56 days.

(21) Appl. No.: 16/955,434

(22) PCT Filed: Jan. 9, 2018

(86) PCT No.: PCT/JP2018/000159
§ 371 (c)(1),
(2) Date: Jun. 18, 2020

(87) PCT Pub. No.: WO2019/138439
PCT Pub. Date: Jul. 18, 2019

(65) Prior Publication Data
US 2020/0348236 A1 Nov. 5, 2020

(51) Int. Cl.
*G01N 21/64* (2006.01)
*G01N 33/00* (2006.01)

(52) U.S. Cl.
CPC ..... *G01N 21/6486* (2013.01); *G01N 33/0098* (2013.01)

(58) Field of Classification Search
CPC .............. G01N 21/6486; G01N 33/0098
See application file for complete search history.

(56) References Cited

U.S. PATENT DOCUMENTS

| | | | |
|---|---|---|---|
| 2003/0112423 A1 | 6/2003 | Vig et al. | |
| 2010/0043104 A1 | 2/2010 | Waga et al. | |
| 2011/0117025 A1* | 5/2011 | Dacosta | A61B 5/72 424/9.6 |
| 2013/0273559 A1* | 10/2013 | Tousch | G01N 21/6486 435/7.1 |

(Continued)

FOREIGN PATENT DOCUMENTS

| | | |
|---|---|---|
| JP | 9-160497 A | 6/1997 |
| JP | 2000-245469 A | 9/2000 |
| JP | 2006-505422 A | 2/2006 |

(Continued)

OTHER PUBLICATIONS

Search Report dated Apr. 3, 2018 issued by the Int. Searching Authority in Application No. PCT/JP2018/000159 (PCT/ISA/210).

*Primary Examiner* — Blake C Riddick
(74) *Attorney, Agent, or Firm* — Sughrue Mion, PLLC

(57) ABSTRACT

An object of the present invention is to provide a means for confirming whether a plant (for example, cannabis or tobacco) or a processed product thereof is a genuine product. The present invention provides a confirmation method including: an irradiation step (S11) of irradiating a plant or a processed product of the plant with light; a confirmation 5 step (S12) of confirming whether the plant or the processed product of the plant irradiated with light emits fluorescence; and a determination step (S13) of determining the plant or the processed product of the plant emitting fluorescence to be a genuine product and the plant or the processed product of the plant not emitting fluorescence to be a counterfeit product.

8 Claims, 9 Drawing Sheets

(56) References Cited

U.S. PATENT DOCUMENTS

2017/0107533 A1    4/2017   Takakura et al.
2017/0246323 A1*   8/2017   Tomalia ............... C07D 207/28

FOREIGN PATENT DOCUMENTS

| JP | 2006-192706 A | 7/2006 |
| JP | 4719226 B2 | 7/2011 |
| JP | 4741994 B2 | 8/2011 |
| JP | 4863280 B2 | 1/2012 |
| WO | 2015/199242 A1 | 12/2015 |

* cited by examiner

CONFIRMATION APPARATUS, CONFIRMATION METHOD, AND NON-TRANSITORY STORAGE MEDIUM

TECHNICAL FIELD

The present invention relates to a confirmation apparatus, a confirmation method, and a program.

BACKGROUND ART

PTL 1 discloses a creation method of horticultural plants in which fluorescent protein originating in marine zooplankton is expressed in a recombinant manner and fluorescence caused by the fluorescent protein is emitted at each piece of tissue of an adult plant, and horticultural plants that are produced using the method.

PTL 2 discloses novel fluorescent protein and a gene coding the fluorescent protein.

PTL 3 discloses a method for modifying a fluorescence wavelength of fluorescent protein and modified fluorescent protein acquired by applying the method.

CITATION LIST

Patent Literature

[PTL 1] Japanese Patent No. 4741994
[PTL 2] Japanese Patent No. 4863280
[PTL 3] Japanese Patent No. 4719226

SUMMARY OF INVENTION

Technical Problem

A means for confirming whether a plant (for example, cannabis or tobacco) or a processed product of the plant that is produced, sold, possessed, and the like is a genuine product has been expected. For example, a means for managing a plant or a processed product of the plant by providing the plant or the processed product of the plant with a bar-code is conceivable. However, in the case of the means, obstructive behavior, such as removal or counterfeiting of a bar-code, makes proper management difficult.

A problem to be solved by the present invention is to provide a means for confirming whether a plant (for example, cannabis or tobacco) or a processed product thereof is a genuine product.

Solution to Problem

According to the present invention,
a confirmation method including:
an irradiation step of irradiating a plant or a processed product of a plant with light;
a confirmation step of confirming whether the plant or the processed product of the plant irradiated with light emits fluorescence; and
a determination step of determining the plant or the processed product of the plant that emits fluorescence to be a genuine product and the plant or the processed product of the plant that does not emit fluorescence to be a counterfeit product is provided.

According to the present invention,
a confirmation apparatus including:
an irradiation unit that irradiates a plant or a processed product of a plant with light;
a confirmation unit that confirms whether the plant or the processed product of the plant irradiated with light emits fluorescence; and
a determination unit that determines the plant or the processed product of the plant that emits fluorescence to be a genuine product and the plant or the processed product of the plant that does not emit fluorescence to be a counterfeit product is provided.

According to the present invention,
a program causing a computer to function as:
an irradiation unit that irradiates a plant or a processed product of a plant with light;
a confirmation unit that confirms whether the plant or the processed product of the plant irradiated with light emits fluorescence; and
a determination unit that determines the plant or the processed product of the plant that emits fluorescence to be a genuine product and the plant or the processed product of the plant that does not emit fluorescence to be a counterfeit product is provided.

Advantageous Effects of Invention

The present invention enables a means for confirming whether a plant (for example, cannabis or tobacco) or a processed product thereof is a genuine product to be achieved.

BRIEF DESCRIPTION OF DRAWINGS

The above-described object and other objects, features, and advantages will be more apparent by the preferred example embodiments described below and the following drawings accompanying therewith.

EXAMPLE EMBODIMENT

First Example Embodiment

An outline of a confirmation method of the present example embodiment will be described. First, a plant or a processed product of the plant that is a genuine product is genetically modified in such a way as to emit fluorescence when being irradiated with light. A plant or a processed product of the plant that is a target of confirmation of whether being a genuine product is irradiated with light, and the plant or the processed product of the plant that emits fluorescence is determined to be a genuine product and the plant or the processed product of the plant that does not emit fluorescence is determined to be a counterfeit product.

Figure 1:
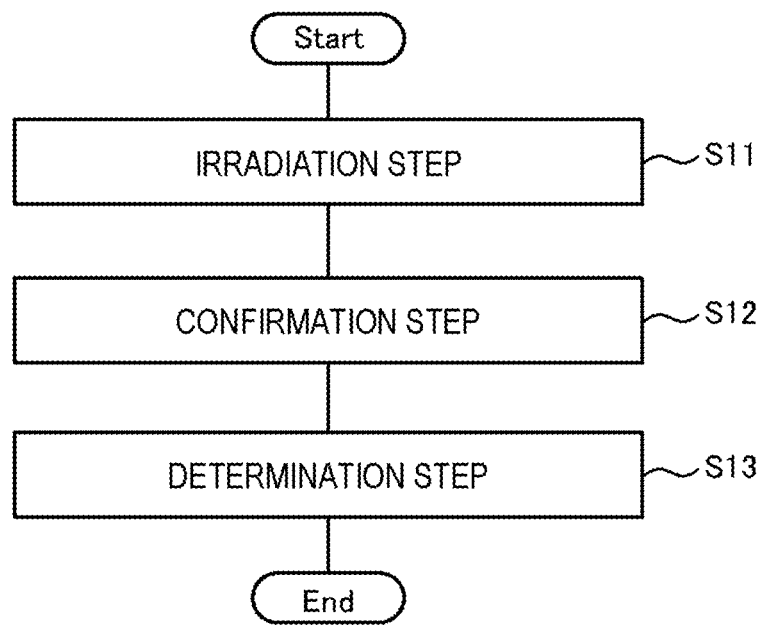
FIG. 1 is a flowchart illustrating an example of a process flow of a confirmation method of the present example embodiment.

Next, a configuration of the confirmation method of the present example embodiment will be described in detail. A flowchart in FIG. 1 illustrates an example of a process flow of the confirmation method of the present example embodiment. As illustrated in the drawing, the confirmation method of the present example embodiment includes an irradiation step S11, a confirmation step S12, and a determination step S13.

In the irradiation step S11, a plant or a processed product of the plant that is a target of confirmation of whether being a genuine product is irradiated with light. Hereinafter, a plant or a processed product of the plant that is a target of confirmation of whether being a genuine product is sometimes referred to as a "confirmation target".

Although examples of a plant that is a target of confirmation of whether being a genuine product include cannabis, tobacco, and the like, the target is not limited to the examples. A legal plant may be categorized as a genuine product, or a brand-name variety that is grown in such a way as to satisfy a criterion may be categorized as a genuine product.

As described above, a plant or a processed product of the plant that is a genuine product is genetically modified in such a way as to emit fluorescence when being irradiated with light. The precondition applies to all the following example embodiments. It should be noted that, such a genetic modification can be achieved using technologies described in, for example, PTLs 1 to 3.

In the present example embodiment, a person irradiates a confirmation target with light. For example, the person may bring the confirmation target to a place where a light is available and irradiate the confirmation target with light at the place. Alternatively, the person may bring a light to a place where the confirmation target is placed and irradiate the confirmation target with light at the place. It should be noted that, in order to confirm fluorescence, the irradiation step S11 is preferably performed in the dark.

In the confirmation step S12, it is confirmed whether the confirmation target irradiated with light emits fluorescence. In the present example embodiment, the person performs the confirmation of whether the confirmation target emits fluorescence. That is, the person visually checks the confirmation target irradiated with light and confirms with his/her own eyes whether the confirmation target emits fluorescence. It should be noted that, the confirmation with his/her own eyes may be performed by directly observing the confirmation target or by observing, through a monitor, the confirmation target being captured by a camera or the like.

In the determination step S13, the confirmation target that emits fluorescence is determined to be a genuine product, and the confirmation target that does not emit fluorescence is determined to be a counterfeit product. In the present example embodiment, the person performs the determination, based on a confirmation result in the confirmation step S12.

Examples of a situation in which it is confirmed whether a confirmation target is a genuine product will be described below.

(1) For example, a plant or a processed product of the plant that a producer and processor who, for example, produces and processes plants or processed products of the plants possesses can be specified as a confirmation target.

A growing plant may be specified as a confirmation target periodically, and whether the plant is a genuine product may be confirmed. Alternatively, a plant that is to be routed to a processing process may be specified as a confirmation target before the processing process, and whether the plant is a genuine product may be confirmed. Still alternatively, a plant or a processed product (finished product) of the plant before being turned over to another business or person (before being released into a distribution channel) may be specified as a confirmation target, and whether the plant or the processed product of the plant is a genuine product may be confirmed.

Confirmation of whether a plant or a processed product of the plant is a genuine product in such situations enables a difficulty in which a producer and processor breeds or processes a counterfeit product to be suppressed. A difficulty in which a counterfeit product falls into the possession of other businesses or persons can also be suppressed.

Figure 2:
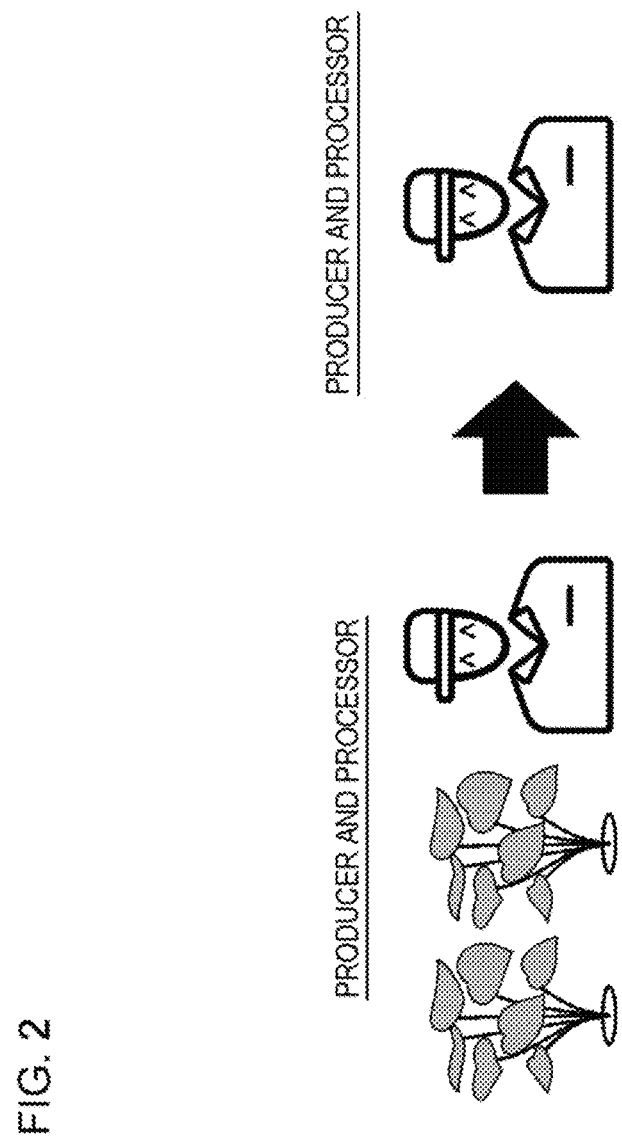
FIG. 2 is a diagram for a description of an example of a situation in which confirmation of whether a confirmation target is a genuine product is performed in the confirmation method of the present example embodiment.

(2) FIG. 2 illustrates an example of a distribution channel of a plant or a processed product of the plant. FIG. 2 illustrates a distribution channel through which a plant or a processed product of the plant is sold from a producer and processor of the plant or the processed product of the plant to another producer and processor.

For example, a plant or a processed product of the plant that the producer and processor having purchased the plant or the processed product of the plant possesses can be specified as a confirmation target. A plant or a processed product of the plant immediately after purchase may be specified as a confirmation target. Confirmation of whether a plant or a processed product of the plant is a genuine product in such situations enables a difficulty in which a producer and processor capable of breeding a plant or producing a processed product obtains a counterfeit product to be suppressed.

Figure 3:
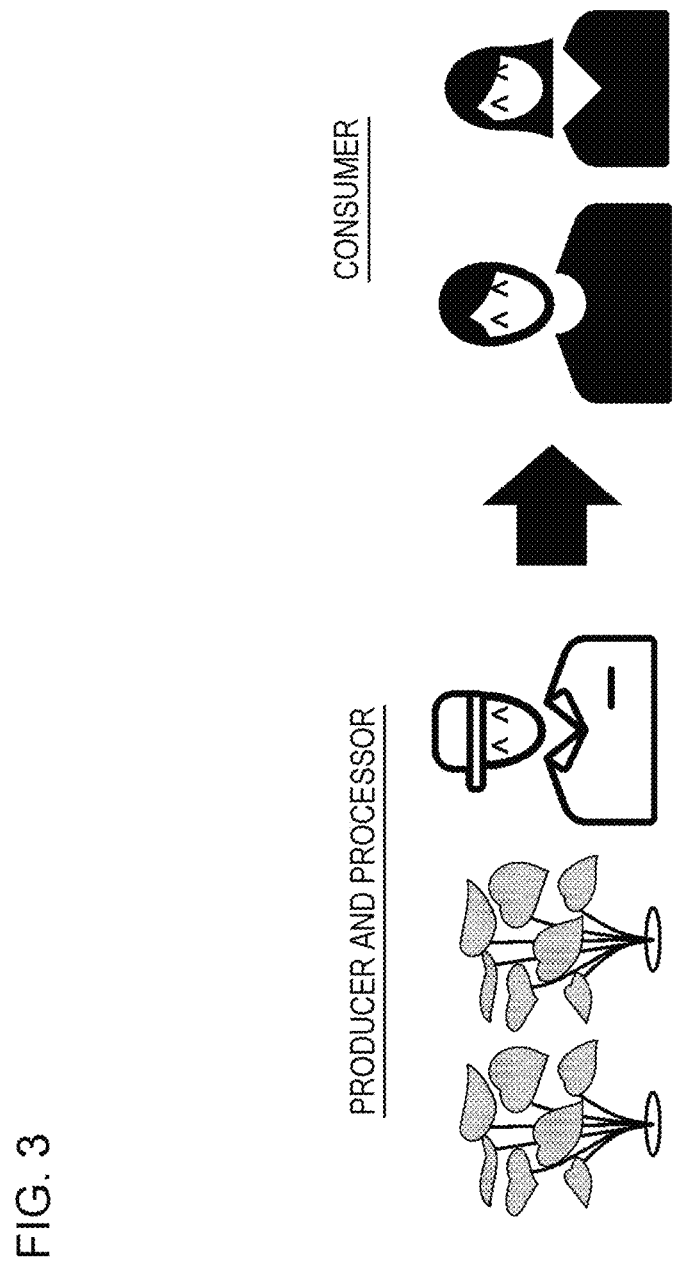
FIG. 3 is a diagram for a description of an example of another situation in which confirmation of whether a confirmation target is a genuine product is performed in the confirmation method of the present example embodiment.

(3) FIG. 3 illustrates another example of a distribution channel of a plant or a processed product of the plant. FIG. 3 illustrates a distribution channel through which a plant or a processed product of the plant is sold from a producer and processor of the plant or the processed product of the plant to consumers.

For example, a plant or a processed product of the plant that a consumer having purchased the plant or the processed product of the plant possesses can be specified as a confirmation target. A plant or a processed product of the plant immediately after purchase may be specified as a confirmation target. Confirmation of whether a plant or a processed product of the plant is a genuine product in such situations enables a difficulty in which a consumer obtains a counterfeit product to be suppressed.

Figure 4:
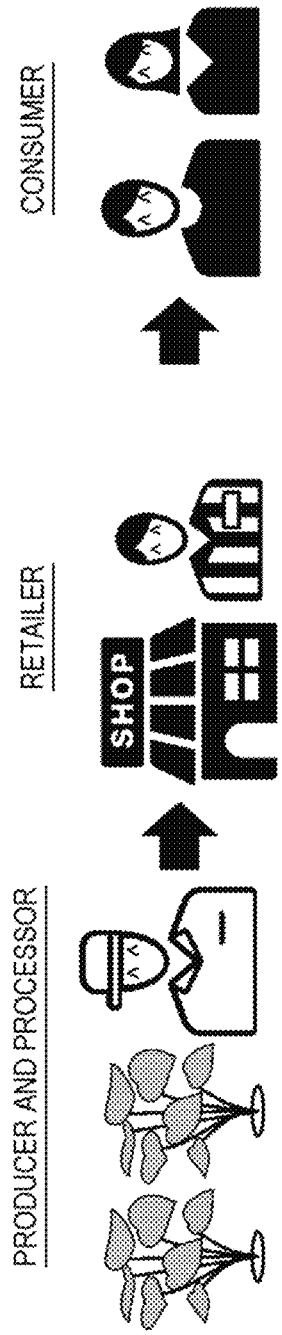
FIG. 4 is a diagram for a description of an example of still another situation in which confirmation of whether a confirmation target is a genuine product is performed in the confirmation method of the present example embodiment.

(4) FIG. 4 illustrates still another example of a distribution channel of a plant or a processed product of the plant. FIG. 4 illustrates a distribution channel through which a plant or a processed product of the plant is sold from a producer and processor of the plant or the processed product of the plant to consumers via a retailer.

For example, a plant or a processed product of the plant that the retailer having purchased the plant or the processed product of the plant possesses can be specified as a confirmation target. A plant or a processed product of the plant immediately after purchase may be specified as a confirmation target. Alternatively, a plant or a processed product of the plant on sale may be specified as a confirmation target. Confirmation of whether a plant or a processed product of the plant is a genuine product in such situations enables a difficulty in which a retailer obtains a counterfeit product or a difficulty in which counterfeit products are widely sold by a retailer to be suppressed.

Figure 5:
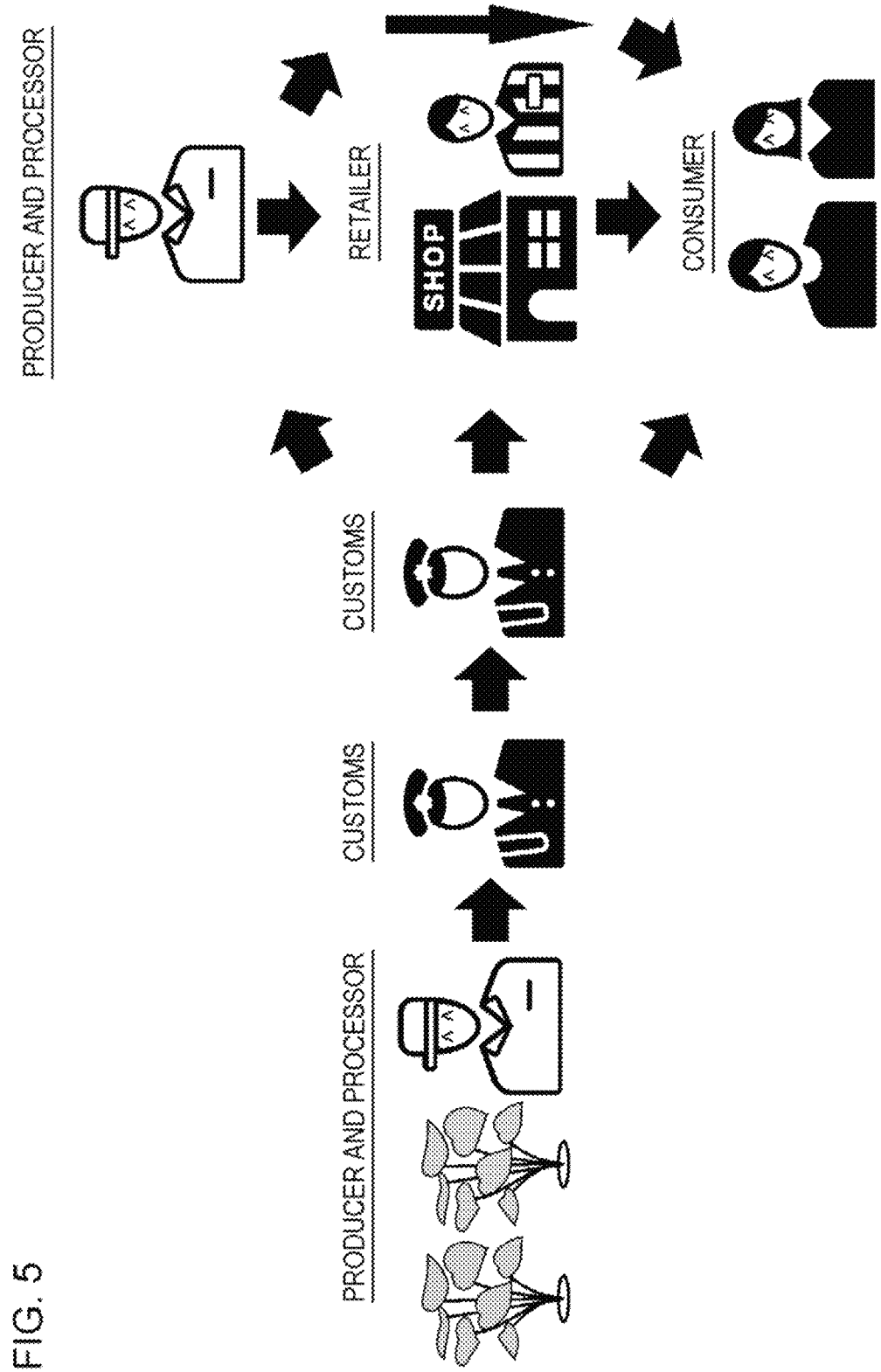
FIG. 5 is a diagram for a description of an example of still another situation in which confirmation of whether a confirmation target is a genuine product is performed in the confirmation method of the present example embodiment.

(5) FIG. 5 illustrates still another example of a distribution channel of a plant or a processed product of the plant. FIG. 5 illustrates a distribution channel through which a plant or a processed product of the plant is sold from a producer and processor of the plant or the processed product of the plant to a foreign producer and processor, a foreign retailer, and foreign consumers via customs.

For example, a plant or a processed product of the plant that passes through customs can be specified as a confirmation target. Confirmation of whether a plant or a processed product of the plant is a genuine product in such a situation enables a difficulty in which counterfeit products go abroad or a difficulty in which counterfeit products enter the country to be suppressed.

The confirmation method of the present example embodiment that has been described thus far enables whether a plant or a processed product of the plant is a genuine product to be confirmed In the confirmation method of the present example embodiment, by giving a predetermined characteristic (emitting fluorescence when being irradiated with light) to a plant or a processed product of the plant by means of genetic modification and confirming whether the plant or the processed product of the plant has the characteristic, it is confirmed whether the plant or the processed product of the plant is a genuine product. The confirmation method of the present example embodiment as described above makes obstructive behavior of causing a counterfeit product to be falsely recognized as a genuine product or obstructive behavior of causing a genuine product to be falsely recognized as a counterfeit product difficult. As a result, it is possible to perform confirmation of whether a plant or a processed product of the plant is a genuine product with high precision.

In the confirmation method of the present example embodiment, it is possible to perform confirmation of whether a plant or a processed product of the plant is a genuine product with high precision through a simple operation of irradiating a confirmation target with light and confirming whether the confirmation target emits fluorescence. Since the operation is simple, it is possible to easily perform the operation whenever and wherever the operation is needed. Thus, it is possible to set a larger quantity of plants or processed products of the plants as confirmation targets and perform confirmation of whether the confirmation targets are genuine products.

Second Example Embodiment

In the present example embodiment, a plant or a processed product of the plant that is a genuine product is genetically modified in such a way as to emit fluorescence when being irradiated with "light of a predetermined wavelength". In a confirmation method of the present example embodiment, a confirmation target is irradiated with the "light of the predetermined wavelength", and the confirmation target that emits fluorescence is determined to be a genuine product and the confirmation target that does not emit fluorescence is determined to be a counterfeit product.

A flowchart in FIG. 1 illustrates an example of a process flow of the confirmation method of the present example embodiment. As illustrated in the drawing, the confirmation method of the present example embodiment includes an irradiation step S11, a confirmation step S12, and a determination step S13.

In the irradiation step S11, a confirmation target is irradiated with the "light of the predetermined wavelength". The light of the predetermined wavelength may be blue light, black light, or ultraviolet rays or may be light of another wavelength. The other configuration of the irradiation step S11 is the same as that of the first example embodiment.

In the confirmation step S12, it is confirmed whether the confirmation target irradiated with the light of the predetermined wavelength emits fluorescence. The other configuration of the confirmation step S12 is the same as that of the first example embodiment.

In the determination step S13, the confirmation target that emits fluorescence when being irradiated with the light of the predetermined wavelength is determined to be a genuine product, and the confirmation target that does not emit fluorescence when being irradiated with the light of the predetermined wavelength is determined to be a counterfeit product. The other configuration of the determination step S13 is the same as that of the first example embodiment.

The confirmation method of the present example embodiment that has been described thus far enables advantageous effects similar to those of the first example embodiment to be achieved. Making more restrictive the condition for emitting fluorescence enables a difficulty in which a forged product (counterfeit product) having similar characteristics to a genuine product is produced, or the like to be suppressed.

Third Example Embodiment

In the present example embodiment, a plant or a processed product of the plant that is a genuine product is genetically modified in such a way as to "emit fluorescence from a predetermined portion" when being irradiated with light. In the confirmation method of the present example embodiment, a plant or a processed product of the plant that is a target of confirmation of whether being a genuine product is irradiated with light, and the plant or the processed product of the plant that emits fluorescence from the predetermined portion is determined to be a genuine product and the plant or the processed product of the plant that does not emit fluorescence from the predetermined portion is determined to be a counterfeit product.

It should be noted that, when the technologies in PTLs 1 to 3 are used, fluorescence is emitted from a random portion in the flower, the leaves, the stem, or the like. For example, hybridizing plants emitting fluorescence from the same portions with each other enables a portion from which fluorescence is emitted to be controlled.

A flowchart in FIG. 1 illustrates an example of a process flow of the confirmation method of the present example embodiment. As illustrated in the drawing, the confirmation method of the present example embodiment includes an irradiation step S11, a confirmation step S12, and a determination step S13.

The irradiation step S11 is the same as those of the first and second example embodiments.

In the confirmation step S12, it is confirmed whether fluorescence is emitted from the predetermined portion of a confirmation target irradiated with light. The "portion that emits fluorescence" to be confirmed in this step is not a portion that emits light when the confirmation target is in a steady state, but a portion that emits light when the confirmation target is irradiated with light. The other configuration of the confirmation step S12 is the same as those of the first and second example embodiments.

In the determination step S13, the confirmation target that emits fluorescence from the predetermined portion is determined to be a genuine product, and the confirmation target that does not emit fluorescence from the predetermined portion is determined to be a counterfeit product. The other configuration of the determination step S13 is the same as those of the first and second example embodiments.

The confirmation method of the present example embodiment that has been described thus far enables advantageous effects similar to those of the first example embodiment to be achieved. Making more restrictive the condition for emitting fluorescence enables a difficulty in which a forged product (counterfeit product) having similar characteristics to a genuine product is produced, or the like to be suppressed.

Fourth Example Embodiment

In the present example embodiment, a plant or a processed product of the plant that is a genuine product is genetically modified in such a way as "to emit fluorescence from a predetermined portion and not to emit fluorescence from another predetermined portion" when being irradiated with light. In the confirmation method of the present example embodiment, a plant or a processed product of the plant that is a target of confirmation of whether being a genuine product is irradiated with light, and the plant or the processed product of the plant that emits fluorescence from the predetermined portion and does not emit fluorescence from another predetermined portion is determined to be a genuine product and the plant or the processed product of the plant reacting otherwise is determined to be a counterfeit product.

For example, a plant or a processed product of the plant can be controlled to emit fluorescence from a predetermined portion by means of the method described in the third example embodiment. By, for example, destroying proteins in a predetermined location by means of heat treatment by laser or the like, a predetermined portion that does not emit fluorescence can be formed. Alternatively, formation of a portion emitting fluorescence and another portion not emitting fluorescence may be controlled by hybridizing a plant emitting fluorescence from a predetermined portion and a plant not emitting fluorescence from a predetermined portion with each other. For example, the portion emitting fluorescence may be located in any of the flower, the leaves, and the stem. The portion not emitting fluorescence may be a portion different from the portion emitting fluorescence in one of the flower, the leaves, and the stem.

A flowchart in FIG. 1 illustrates an example of a process flow of the confirmation method of the present example embodiment. As illustrated in the drawing, the confirmation method of the present example embodiment includes an irradiation step S11, a confirmation step S12, and a determination step S13.

The irradiation step S11 is the same as those of the first to third example embodiments.

In the confirmation step S12, it is confirmed whether a confirmation target irradiated with light emits fluorescence from the predetermined portion and does not emit fluorescence from another predetermined portion. The "portion that emits fluorescence" to be confirmed in this step is not a portion that emits light when the confirmation target is in a steady state, but a portion that emits light when the confirmation target is irradiated with light. The "portion that does not emit fluorescence" to be confirmed in this step is not a portion that does not emit light when the confirmation target is in a steady state, but a portion that does not emit light when the confirmation target is irradiated with light. The other configuration of the confirmation step S12 is the same as those of the first to third example embodiments.

In the determination step S13, the confirmation target that emits fluorescence from the predetermined portion and does not emit fluorescence from another predetermined potion is determined to be a genuine product, and the confirmation target that reacts otherwise is determined to be a counterfeit product. The other configuration of the determination step S13 is the same as those of the first to third example embodiments.

The confirmation method of the present example embodiment that has been described thus far enables advantageous effects similar to those of the first example embodiment to be achieved. Making more restrictive the condition for emitting fluorescence enables a difficulty in which a forged product (counterfeit product) having similar characteristics to a genuine product is produced, or the like to be suppressed.

Fifth Example Embodiment

In the present example embodiment, a plant or a processed product of the plant that is a genuine product is genetically modified in such a way as to "emit fluorescence of a predetermined color" when being irradiated with light. In the confirmation method of the present example embodiment, a confirmation target is irradiated with light, and the confirmation target that emits fluorescence of the predetermined color is determined to be a genuine product and the confirmation target that does not emit fluorescence of the predetermined color is determined to be a counterfeit product.

A flowchart in FIG. 1 illustrates an example of a process flow of the confirmation method of the present example embodiment. As illustrated in the drawing, the confirmation method of the present example embodiment includes an irradiation step S11, a confirmation step S12, and a determination step S13.

The irradiation step S11 is the same as those of the first to fourth example embodiments.

In the confirmation step S12, it is confirmed whether a confirmation target irradiated with light emits fluorescence of the predetermined color. The "color of fluorescence" to be confirmed in this step is not a color of fluorescence when the confirmation target is in a steady state, but a color of fluorescence that is emitted when the confirmation target is irradiated with light. The other configuration of the confirmation step S12 is the same as those of the first to fourth example embodiments.

In the determination step S13, the confirmation target that emits fluorescence of the predetermined color is determined to be a genuine product, and the confirmation target that does not emit fluorescence of the predetermined color is determined to be a counterfeit product. The other configuration of the determination step S13 is the same as those of the first to fourth example embodiments.

The confirmation method of the present example embodiment that has been described thus far enables advantageous effects similar to those of the first example embodiment to be achieved. Making more restrictive the condition for emitting fluorescence enables a difficulty in which a forged product (counterfeit product) having similar characteristics to a genuine product is produced, or the like to be suppressed.

Sixth Example Embodiment

In the present example embodiment, a plant or a processed product of the plant that is a genuine product is genetically modified in such a way as to "emit fluorescence of an intensity equal to or more than a threshold value" when being irradiated with light. In the confirmation method of the present example embodiment, a confirmation target is irradiated with light, and the confirmation target that emits fluorescence of the intensity equal to or more than the threshold value is determined to be a genuine product and the confirmation target reacting otherwise is determined to be a counterfeit product.

A flowchart in FIG. 1 illustrates an example of a process flow of the confirmation method of the present example embodiment. As illustrated in the drawing, the confirmation method of the present example embodiment includes an irradiation step S11, a confirmation step S12, and a determination step S13.

The irradiation step S11 is the same as those of the first to fifth example embodiments.

In the confirmation step S12, it is confirmed whether a confirmation target irradiated with light emits fluorescence of the intensity equal to or more than the threshold value. The "intensity of fluorescence" to be confirmed in this step is not an intensity of fluorescence when the confirmation target is in a steady state, but an intensity of fluorescence that is emitted when the confirmation target is irradiated with light. The other configuration of the confirmation step S12 is the same as those of the first to fifth example embodiments.

In the determination step S13, the confirmation target that emits fluorescence of the intensity equal to or more than the threshold value is determined to be a genuine product, and the confirmation target reacting otherwise is determined to be a counterfeit product. The other configuration of the determination step S13 is the same as those of the first to fifth example embodiments.

The confirmation method of the present example embodiment that has been described thus far enables advantageous effects similar to those of the first example embodiment to be achieved. Making more restrictive the condition for fluorescence emitted enables a difficulty in which a forged product (counterfeit product) having similar characteristics to a genuine product is produced, or the like to be suppressed.

Seventh Example Embodiment

In the present example embodiment, a plant or a processed product of the plant that is a genuine product is genetically modified in such a way as to satisfy at least one of conditions that the plant or the processed product of the plant, "emits fluorescence when being irradiated with light of a predetermined wavelength", "emits fluorescence from a predetermined portion", "emits fluorescence from a predetermined portion and does not emit fluorescence from another predetermined portion", "emits fluorescence of a predetermined color", and "emits fluorescence of an intensity equal to or more than a threshold value". In the present example embodiment, a confirmation target that satisfies the above-described condition for determination as a genuine product is determined to be a genuine product, and a confirmation target that does not emit fluorescence is determined to be a counterfeit product. The present example embodiment can be achieved in a similar manner to those of the first to sixth example embodiments.

The confirmation method of the present example embodiment that has been described thus far enables advantageous effects similar to those of the first to sixth example embodiments to be achieved.

Eighth Example Embodiment

In the present example embodiment, genuine products are divided into a plurality of groups. For example, genuine products may be divided for each area of production or for each production period or divided based on another criterion. A characteristic given to genuine products in each group is differentiated. For example, at least one of "a wavelength of light radiated to cause fluorescence to be emitted", "a portion emitting fluorescence", "a portion emitting fluorescence and another portion not emitting fluorescence", "a color of fluorescence", and "an intensity of fluorescence" is differentiated.

In the present example embodiment, characteristic information indicating a characteristic given to each genuine product is provided to the genuine product. For example, a code (for example, a bar-code or a two-dimensional code) indicating characteristic information may be provided to a plant or a processed product of the plant or an integrated circuit (IC) chip storing characteristic information may be provided to a plant or a processed product of the plant. In the confirmation method of the present example embodiment, characteristic information given to each plant or processed product of the plant is acquired, and, based on the acquired characteristic information, it is confirmed whether the plant or the processed product of the plant is a genuine product.

Figure 6:
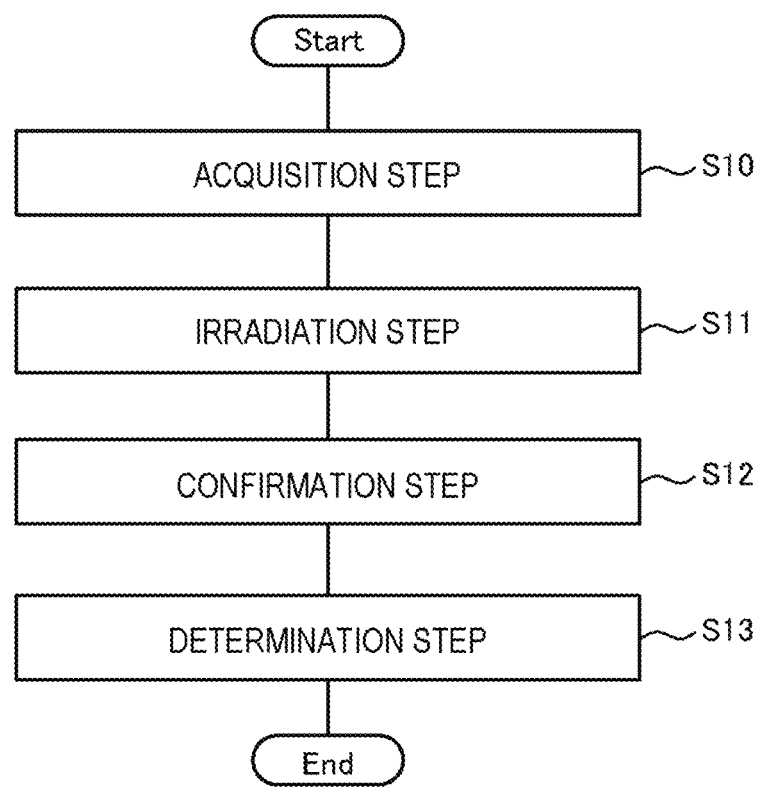
FIG. 6 is a flowchart illustrating an example of a process flow of a confirmation method of the present example embodiment.

A flowchart in FIG. 6 illustrates an example of a process flow of the confirmation method of the present example embodiment. As illustrated in the drawing, the confirmation method of the present example embodiment includes an acquisition step S10, an irradiation step S11, a confirmation step S12, and a determination step S13. It should be noted that, the position of the acquisition step S10 in the execution sequence is not limited to that illustrated in the drawing, and the acquisition step S10 may be performed at another timing.

In the acquisition step S10, a person acquires characteristic information given to a confirmation target. For example, a code (for example, a bar-code or a two-dimensional code) indicating characteristic information may be provided to a confirmation target. In this case, the person causes a code reader to read the code and visually checks a reading result (characteristic information) output from a predetermined output devise (for example, a display). Alternatively, an IC chip storing characteristic information may be provided to a confirmation target. In this case, by bringing a reader and the IC chip into a communicable state (for example, into proximity or into contact) with each other, the person causes the reader to acquire characteristic information stored in the IC chip and visually recognizes characteristic information output from a predetermined output apparatus (for example, a display).

The characteristic information may include at least one of information (wavelength information) indicating a wavelength of light radiated to cause fluorescence to be emitted, information (first fluorescent portion information) indicating a portion emitting fluorescence, information (second fluorescent portion information) indicating a portion emitting fluorescence and another portion not emitting fluorescence, information (fluorescence color information) indicating a color of emitted fluorescence, and information (fluorescence intensity information) indicating an intensity of emitted fluorescence.

When the characteristic information includes the wavelength information, in the irradiation step S11, the person irradiates the confirmation target with light of a wavelength indicated by the wavelength information. In the confirmation step S12, the person confirms whether the confirmation target irradiated with the light of the wavelength indicated by the wavelength information emits fluorescence. In the determination step S13, the person determines the confirmation target that emits fluorescence when being irradiated with the light of the wavelength indicated by the wavelength information to be a genuine product and the confirmation target that does not emit fluorescence when being irradiated with the light of the wavelength indicated by the wavelength information to be a counterfeit product.

When the characteristic information includes the first fluorescent portion information, in the confirmation step S12, the person confirms whether the confirmation target emits fluorescence from a portion to emit fluorescence indicated by the first fluorescent portion information. In the determination step S13, the person determines the confirmation target that emits fluorescence from the portion to emit fluorescence indicated by the first fluorescent portion information to be a genuine product and the confirmation target that does not emit fluorescence from the portion to emit fluorescence indicated by the first fluorescent portion information to be a counterfeit product.

When the characteristic information includes the second fluorescent portion information, in the confirmation step S12, the person confirms whether the confirmation target emits fluorescence from a portion to emit fluorescence indicated by the second fluorescent portion information and the confirmation target does not emit fluorescence from another portion not to emit fluorescence indicated by the second fluorescent portion information. In the determination step S13, the person determines the confirmation target that emits fluorescence from the portion to emit fluorescence indicated by the second fluorescent portion information and does not emit fluorescence from another portion not to emit fluorescence indicated by the second fluorescent portion information to be a genuine product and the confirmation target reacting otherwise to be a counterfeit product.

When the characteristic information includes the fluorescence color information, in the confirmation step S12, the person confirms whether the confirmation target emits fluorescence of a color indicated by the fluorescence color information. In the determination step S13, the person determines the confirmation target that emits fluorescence of the color indicated by the fluorescence color information to be a genuine product and the confirmation target that does not emit fluorescence of the color indicated by the fluorescence color information to be a counterfeit product.

When the characteristic information includes the fluorescence intensity information, in the confirmation step S12, the person confirms whether the confirmation target emits fluorescence of an intensity indicated by the fluorescence intensity information. In the determination step S13, the person determines the confirmation target that emits fluorescence of the intensity indicated by the fluorescence intensity information to be a genuine product and the confirmation target reacting otherwise to be a counterfeit product.

The other configurations of the irradiation step S11, the confirmation step S12, and the determination step S13 are the same as those of the first to seventh example embodiments.

The confirmation method of the present example embodiment that has been described thus far enables advantageous effects similar to those of the first to seventh example embodiments to be achieved.

Dividing genuine products into a plurality of groups and differentiating characteristics given to genuine products in each group enable the genuine products to be managed more finely. Characteristic information indicating a characteristic given to each plant or processed product of the plant may be provided to the plant or the processed product of the plant. In such a case, it is possible to acquire characteristic information from a confirmation target itself. Thus, it is possible to recognize a characteristic given to each genuine product efficiently and easily.

A variation of the present example embodiment will be described below. Characteristic information indicating a characteristic given to each genuine product may be notified to a person performing confirmation operation in advance by means of other means. For example, the characteristic information may be notified by means of electronic mail or the like. It should be noted that, in the notification to the person performing the confirmation operation, security may be reinforced using passwords or one-time passwords. The variation also enables the same advantageous effects to be achieved.

Ninth Example Embodiment

In the present example embodiment, a computer performs an irradiation step S11, a confirmation step S12, and a determination step S13. Processes performed in the steps are the same as those of the first to eighth example embodiments.

Figure 7:
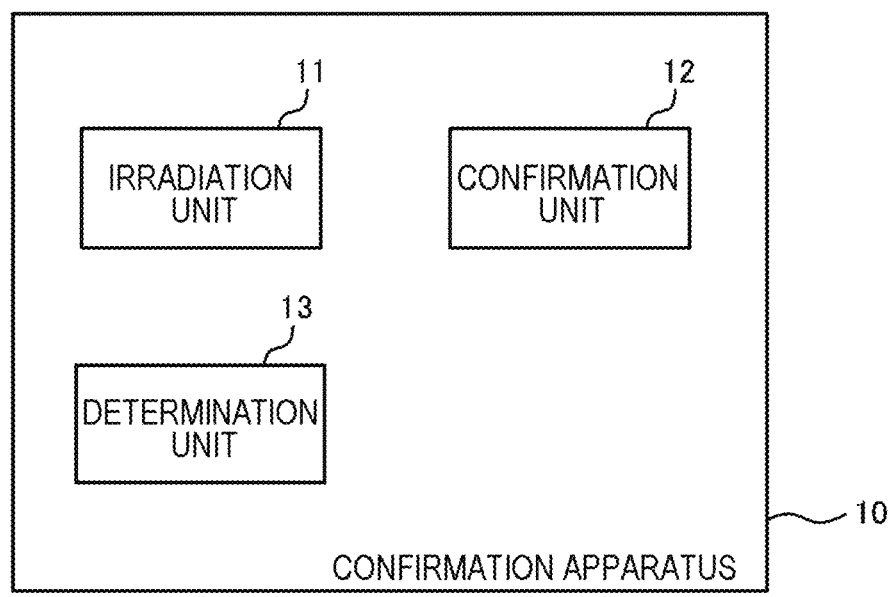
FIG. 7 is a diagram illustrating an example of a functional block diagram of the confirmation apparatus of the present example embodiment.

In FIG. 7, an example of a functional block diagram of a confirmation apparatus 10 that performs the irradiation step S11, the confirmation step S12, and the determination step S13 is illustrated. As illustrated in the drawing, the confirmation apparatus 10 includes an irradiation unit 11, a confirmation unit 12, and a determination unit 13.

First, an example of a hardware configuration of the confirmation apparatus 10 will be described. The units that the confirmation apparatus 10 of the present example embodiment includes are achieved by any combination of hardware and software, which mainly include a central processing unit (CPU), a memory, programs that are loaded in the memory, a storage unit, such as a hard disk, that stores the programs (the storage unit can store not only a program that has been stored in advance since a shipment stage of the apparatus but also a program that is downloaded from a storage medium, such as a compact disc (CD), or a server or the like on the Internet), and an interface for network connection in any computer. It should be understood by those skilled in the art that there are various variations for a method and an apparatus to achieve the units.

Figure 8:
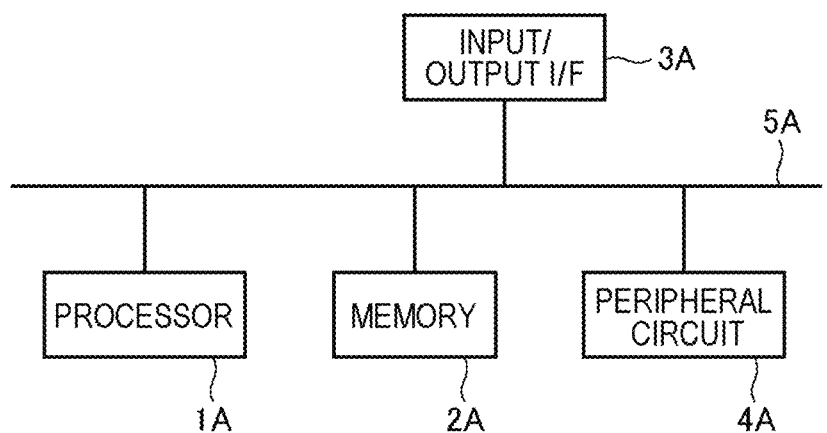
FIG. 8 is a diagram illustrating an example of a hardware configuration of the confirmation apparatus of the present example embodiment.

FIG. 8 is a block diagram illustrating a hardware configuration of the confirmation apparatus 10 of the present example embodiment. As illustrated in FIG. 8, the confirmation apparatus 10 includes a processor 1A, a memory 2A, an input/output interface 3A, a peripheral circuit 4A, and a bus 5A. In the peripheral circuit 4A, various modules are included. It should be noted that, the confirmation apparatus 10 does not have to include the peripheral circuit 4A.

The bus 5A is a data transmission line through which the processor 1A, the memory 2A, the peripheral circuit 4A, and the input/output interface 3A transmit and receive data to and from one another. The processor 1A is an arithmetic processing apparatus, such as a central processing unit (CPU) and a graphics processing unit (GPU). The memory 2A is a memory, such as a random access memory (RAM) and a read only memory (ROM). The input/output interface 3A includes, for example, an interface for acquiring information from an input apparatus (such as a keyboard, a mouse, and a microphone), an external apparatus, an external server, an external sensor, or the like and an interface for outputting information to an output apparatus (such as a display, a speaker, a printer, and a mailer), an external apparatus, an external server, or the like. The processor 1A can send commands to the modules and perform calculation, based on calculation results of the modules.

The irradiation unit 11 performs the irradiation step S11. The irradiation step S11 is the same as those of the first to eighth example embodiments. For example, the irradiation unit 11 may radiate light in response to an input by an operator. Alternatively, the irradiation unit 11 may detect that a confirmation target is located at an irradiation location. Then, the irradiation unit 11 may radiate light in response to the detection. The detection may be achieved by means of, for example, image analysis or achieved using any sensor.

The confirmation unit 12 performs the confirmation step S12. The confirmation step S12 is the same as those of the first to eighth example embodiments. The confirmation unit 12 performs, by analyzing an image (image analysis) in which a confirmation target irradiated with light is captured, the confirmation process that was described in the first to eighth example embodiments.

The determination unit 13 performs the determination step S13. The determination step S13 is the same as those of the first to eighth example embodiments. The determination unit 13 determines, based on a confirmation result by the confirmation unit 12, whether a confirmation target is a genuine product.

The confirmation apparatus 10 of the present example embodiment that has been described thus far enables advantageous effects similar to those of the first to eighth example embodiments to be achieved. The present example embodiment in which a computer (the confirmation apparatus 10) performs the process steps enables confirmation operation to be performed efficiently and surely.

Tenth Example Embodiment

In the present example embodiment, a computer performs an acquisition step S10, an irradiation step S11, a confirmation step S12, and a determination step S13. Processes performed in the steps are the same as those of the first to ninth example embodiments.

Figure 9:
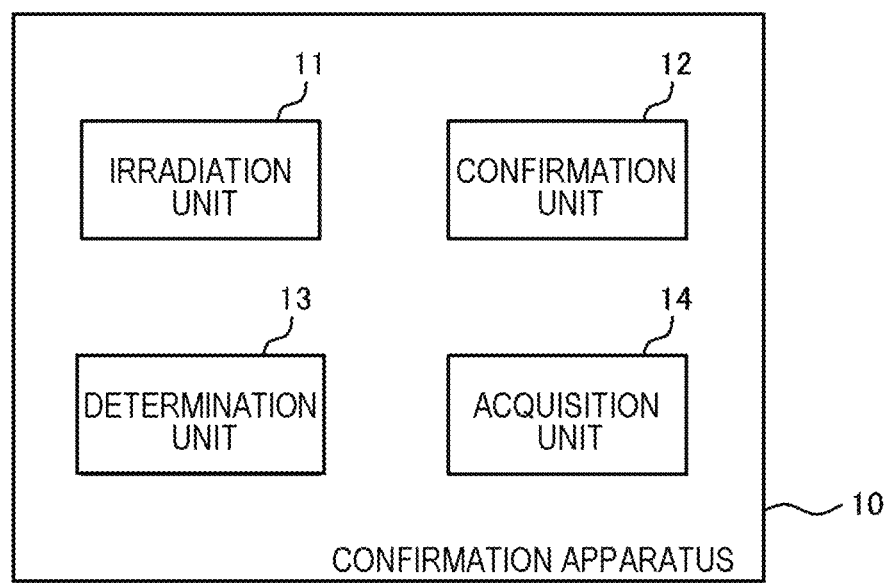
FIG. 9 is a diagram illustrating an example of a functional block diagram of the confirmation apparatus of the present example embodiment.

In FIG. 9, an example of a functional block diagram of a confirmation apparatus 10 that performs the acquisition step S10, the irradiation step S11, the confirmation step S12, and the determination step S13 is illustrated. As illustrated in the drawing, the confirmation apparatus 10 includes an irradiation unit 11, a confirmation unit 12, a determination unit 13, and an acquisition unit 14.

The acquisition unit 14 performs the acquisition step S10. The acquisition step S10 is the same as that of the eighth example embodiment. For example, a code (for example, a bar-code or a two-dimensional code) indicating characteristic information may be provided to a confirmation target. In this case, the confirmation apparatus 10 includes a code reader. A person causing the code reader to read the code causes the acquisition unit 14 to acquire the characteristic information. Alternatively, an IC chip storing characteristic information may be provided to a confirmation target. In this case, the confirmation apparatus 10 includes a reader that performs short-range wireless communication with the IC chip. A person bringing the reader and the IC chip into a communicable state (for example, into proximity or into contact) with each other causes the acquisition unit 14 to acquire characteristic information stored in the IC chip. The acquisition unit 14 stores the acquired characteristic information in a memory of the confirmation apparatus 10. Alternatively, characteristic information indicating a characteristic given to each genuine product may be notified to a person performing confirmation operation in advance by means of other means, such as electronic mail. The person may input the characteristic information in the confirmation apparatus 10 via an input apparatus. It should be noted that, in the notification to the person performing the confirmation operation, security may be reinforced using passwords or one-time passwords.

The characteristic information may include at least one of information (wavelength information) indicating a wavelength of light radiated to cause fluorescence to be emitted, information (first fluorescent portion information) indicating a portion emitting fluorescence, information (second fluorescent portion information) indicating a portion emitting fluorescence and another portion not emitting fluorescence, information (fluorescence color information) indicating a color of emitted fluorescence, and information (fluorescence intensity information) indicating an intensity of emitted fluorescence.

When the characteristic information includes the wavelength information, the irradiation unit 11 irradiates the confirmation target with light of a wavelength indicated by the wavelength information. The confirmation unit 12 confirms, by means of image analysis, whether the confirmation target irradiated with the light of the wavelength indicated by the wavelength information emits fluorescence. The determination unit 13 determines the confirmation target that emits fluorescence when being irradiated with the light of the wavelength indicated by the wavelength information to be a genuine product and the confirmation target that does not emit fluorescence when being irradiated with the light of the wavelength indicated by the wavelength information to be a counterfeit product.

When the characteristic information includes the first fluorescent portion information, the confirmation unit 12 confirms, by means of image analysis, whether the confirmation target emits fluorescence from a portion to emit fluorescence indicated by the first fluorescent portion information. The determination unit 13 determines the confirmation target that emits fluorescence from the portion to emit fluorescence indicated by the first fluorescent portion information to be a genuine product and the confirmation target that does not emit fluorescence from the portion to emit fluorescence indicated by the first fluorescent portion information to be a counterfeit product.

When the characteristic information includes the second fluorescent portion information, the confirmation unit 12 confirms, by means of image analysis, whether the confirmation target emits fluorescence from a portion to emit fluorescence indicated by the second fluorescent portion information and the confirmation target does not emit fluorescence from another portion not to emit fluorescence indicated by the second fluorescent portion information. The determination unit 13 determines the confirmation target that emits fluorescence from the portion to emit fluorescence indicated by the second fluorescent portion information and does not emit fluorescence from another portion not to emit fluorescence indicated by the second fluorescent portion information to be a genuine product and the confirmation target reacting otherwise to be a counterfeit product.

When the characteristic information includes the fluorescence color information, the confirmation unit 12 confirms, by means of image analysis, whether the confirmation target emits fluorescence of a color indicated by the fluorescence color information. The determination unit 13 determines the confirmation target that emits fluorescence of the color indicated by the fluorescence color information to be a genuine product and the confirmation target that does not emit fluorescence of the color indicated by the fluorescence color information to be a counterfeit product.

When the characteristic information includes the fluorescence intensity information, the confirmation unit 12 confirms, by means of image analysis, whether the confirmation target emits fluorescence of an intensity indicated by the fluorescence intensity information. The determination unit 13 determines the confirmation target that emits fluorescence of the intensity indicated by the fluorescence intensity information to be a genuine product, and the confirmation target reacting otherwise to be a counterfeit product.

It should be noted that, the irradiation unit 11 may radiate light only for a certain period in response to a predetermined input. The predetermined input may be an input of a security code, a password, a one-time password, or the like by a person.

The confirmation apparatus 10 of the present example embodiment that has been described thus far enables advantageous effects similar to those of the first to ninth example embodiments to be achieved.

A variation that is applicable to the confirmation apparatus 10 of the ninth and tenth example embodiments will be described below. When the determination unit 13 determines a confirmation target to be a genuine product, the confirmation apparatus 10 may display effectiveness relevant to the confirmation target on the display or the like. When the determination unit 13 determines a confirmation target to be a counterfeit product, the confirmation apparatus 10 may acquire and accumulate location information of the place (counterfeit product discovery place) where the determination is made. The confirmation apparatus 10 may generate map data in which counterfeit product discovery places are mapped and display the map data on the display or the like.

Hereinafter, examples of reference aspects will be additionally stated.

1. A confirmation method including:
   an irradiation step of irradiating a plant or a processed product of a plant with light;
   a confirmation step of confirming whether the plant or the processed product of the plant irradiated with light emits fluorescence; and
   a determination step of determining the plant or the processed product of the plant that emits fluorescence to be a genuine product and the plant or the processed product of the plant that does not emit fluorescence to be a counterfeit product.

2. The confirmation method according to aspect 1,
   in which the plant or the processed product of the plant that is a genuine product is genetically modified in such a way as to emit fluorescence when being irradiated with light.

3. The confirmation method according to aspect 1 or 2,
   in which the plant or the processed product of the plant that is a genuine product emits fluorescence when being irradiated with light of a predetermined wavelength,
   the method further including an acquisition step of acquiring characteristic information indicating the predetermined wavelength, and
   in which in the irradiation step, light of the wavelength indicated by the characteristic information is radiated.

4. The confirmation method according to any one of aspects 1 to 3,
   in which the plant or the processed product of the plant that is a genuine product emits fluorescence from a predetermined portion,
   the method further including an acquisition step of acquiring characteristic information indicating the predetermined portion,
   in which in the confirmation step, a portion that emits fluorescence is confirmed, and
   in which in the determination step, the plant or the processed product of the plant that emits fluorescence from the portion indicated by the characteristic information is determined to be a genuine product and the plant or the processed product of the plant that does not emit fluorescence from the portion indicated by the characteristic information is determined to be a counterfeit product.

5. The confirmation method according to any one of aspects 1 to 4,
   in which the plant or the processed product of the plant that is a genuine product emits fluorescence of a predetermined color,
   the method including an acquisition step of acquiring characteristic information indicating the predetermined color,
   in which in the confirmation step, a fluorescence color is confirmed, and
   in which in the determination step, the plant or the processed product of the plant that emits fluorescence of the color indicated by the characteristic information is determined to be a genuine product and the plant or the processed product of the plant that does not emit fluorescence of the color indicated by the characteristic information is determined to be a counterfeit product.

6. The confirmation method according to any one of aspects 3 to 5,
   in which the characteristic information is given to the plant or the processed product of the plan, and
   in which in the acquisition step, the characteristic information given to the plant or the processed product of the plant is acquired.

7. The confirmation method according to any one of aspects 3 to 5,
   in which in the acquisition step, notification of the characteristic information is received by means of electronic mail.

8. The confirmation method according to any one of aspects 1 to 7,
   in which the steps are performed by a computer.

9. The confirmation method according to aspect 8,
   in which in the confirmation step, image analysis is used.

10. A confirmation apparatus including:
    an irradiation unit that irradiates a plant or a processed product of a plant with light;

a confirmation unit that confirms whether the plant or the processed product of the plant irradiated with light emits fluorescence; and a determination unit that determines the plant or the processed product of the plant that emits fluorescence to be a genuine product and the plant or the processed product of the plant that does not emit fluorescence to be a counterfeit product.

11. A program causing a computer to function as:

an irradiation unit that irradiates a plant or a processed product of a plant with light;

a confirmation unit that confirms whether the plant or the processed product of the plant irradiated with light emits fluorescence; and a determination unit that determines the plant or the processed product of the plant that emits fluorescence to be a genuine product and the plant or the processed product of the plant that does not emit fluorescence to be a counterfeit product.

The invention claimed is:

1. A confirmation method comprising:
an acquisition step of acquiring, from a plant or a processed product of a plant, characteristic information including information about a predetermined wavelength;
an irradiation step of irradiating the plant or the plant-processed product with a light having the predetermined wavelength which is acquired by the acquisition step;
a confirmation step of confirming whether the plant or the plant-processed product irradiated with the light having the predetermined wavelength emits fluorescence;
a determination step of determining, based on a judgement whether or not the plant or the plant-processed product emits the fluorescence in response to the irradiated light having the predetermined wavelength, whether the plant or the plant-processed product is a genuine product or not,
wherein the determination step determines that the plant or the plant-processed product is the genuine product if the plant or the plant-processed product emits the fluorescence in response to the irradiated light having the predetermined wavelength,
wherein the determination step determines that the plant or the plant-processed product is a counterfeit product if the plant or the plant-processed product does not emit the fluorescence in response to the irradiated light having the predetermined wavelength, and
wherein the plant or the plant-processed product that is the genuine product is genetically modified in such a way as to emit the fluorescence from a predetermined portion of the plant or the plant-processed product when being irradiated with the light having the predetermined wavelength,
wherein the characteristic information comprises information about the predetermined portion, and
wherein the confirmation step checks that the predetermined portion of the plant or the plant-processed product emits the fluorescence.

2. The confirmation method according to claim 1,
wherein the plant or the plant-processed product that is the genuine product emits the fluorescence having a predetermined color,
wherein the characteristic information comprises information about the predetermined color,
wherein the confirmation step checks a color of the fluorescence, which is emitted from the plant or the plant-processed product, corresponding to the predetermined color indicated by the characteristic information, and
wherein the determination step determines that the plant or the plant-processed product is the genuine product if the plant or the plant-processed product emits the fluorescence with the predetermined color, and
wherein the determination step determines that the plant or the plant-processed product is the counterfeit product if the plant or the plant-processed product does not emit the fluorescence with the predetermined color.

3. The confirmation method according to claim 1,
wherein the characteristic information is provided to the plant or the plant-processed product, and
wherein the acquisition step acquires the characteristic information provided to the plant or the plant-processed product.

4. The confirmation method according to claim 1,
wherein the acquisition step receives the characteristic information by means of electronic mail.

5. The confirmation method according to claim 1,
wherein the steps are performed by a computer.

6. The confirmation method according to claim 5,
wherein in the confirmation step, image analysis is used.

7. A confirmation apparatus comprising:
a light configured to irradiate a plant or a processed product of a plant with light;
at least one memory configured to store one or more instructions; and
at least one processor configured to execute the one or more instructions to:
analyze a captured image;
acquire, from the plant or the plant-processed product, characteristic information including information about a predetermined wavelength;
cause the light to irradiate the plant or the plant-processed product with the light having the predetermined wavelength which is acquired by the at least one processor;
confirm whether the plant or the plant-processed product irradiated with the light having the predetermined wavelength emits fluorescence;
determine, based on a judgement whether or not the plant or the plant-processed product emits the fluorescence in response to the irradiated light having the predetermined wavelength, whether the plant or the plant-processed product is a genuine product or not,
wherein the determination of whether the plant or the plant-processed product is the genuine product or not comprises determining that the plant or the plant-processed product is the genuine product if the plant or the plant-processed product emits the fluorescence in response to the irradiated light having the predetermined wavelength,
wherein the determination of whether the plant or the plant-processed product is the genuine product or not comprises determining that the plant or the plant-processed product is a counterfeit product if the plant or the plant-processed product does not emit the fluorescence in response to the irradiated light having the predetermined wavelength, and
wherein the plant or the plant-processed product that is the genuine product is genetically modified in such a way as to emit the fluorescence from a predetermined portion of the plant or the plant-processed product when being irradiated with the light having the predetermined wavelength, wherein the characteristic information comprises information about the predetermined portion, and wherein the confirmation step checks that the predetermined portion of the plant or the plant-processed product emits the fluorescence.

8. A non-transitory storage medium storing a program causing a computer to:
- acquire, from a plant or a processed product of a plant, characteristic information including information about a predetermined wavelength;
- cause a light to irradiate the plant or the plant-processed product with a light having the predetermined wavelength which is acquired by the at least one processor;
- confirm whether the plant or the plant-processed product irradiated with the light having the predetermined wavelength emits fluorescence;
- determine, based on a judgement whether or not the plant or the plant-processed product emits the fluorescence in response to the irradiated light having the predetermined wavelength, whether the plant or the plant-processed product is a genuine product or not, wherein the determination of whether the plant or the plant-processed product is the genuine product or not comprises determining that the plant or the plant-processed product is the genuine product if the plant or the plant-processed product emits the fluorescence in response to the irradiated light having the predetermined wavelength, wherein the determination of whether the plant or the plant-processed product is the genuine product or not comprises determining that the plant or the plant-processed product is a counterfeit product if the plant or the plant-processed product does not emit the fluorescence in response to the irradiated light having the predetermined wavelength, and wherein the plant or the plant-processed product that is the genuine product is genetically modified in such a way as to emit the fluorescence from a predetermined portion of the plant or the plant-processed product when being irradiated with the light having the predetermined wavelength, wherein the characteristic information comprises information about the predetermined portion, and wherein the confirmation step checks that the predetermined portion of the plant or the plant-processed product emits the fluorescence.

\* \* \* \* \*